(12) United States Patent
Sasaki et al.

(10) Patent No.: US 8,024,134 B2
(45) Date of Patent: Sep. 20, 2011

(54) GAS SENSOR AND OUTPUT PROCESSING METHOD THEREOF

(75) Inventors: Takashi Sasaki, Wako (JP); Akihiro Suzuki, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 1095 days.

(21) Appl. No.: 11/461,159

(22) Filed: Jul. 31, 2006

(65) Prior Publication Data

US 2007/0028666 A1    Feb. 8, 2007

(30) Foreign Application Priority Data

Aug. 1, 2005  (JP) .................................. 2005-223284

(51) Int. Cl.
*G01B 5/28*  (2006.01)

(52) U.S. Cl. ................. 702/35; 702/34; 702/81; 702/24; 702/31; 702/50; 702/100

(58) Field of Classification Search ............... 702/24, 702/31, 50, 100, 34, 35, 81
See application file for complete search history.

(56) References Cited

U.S. PATENT DOCUMENTS

| | | | | |
|---|---|---|---|---|
| 3,228,027 A | * | 1/1966 | Milnes | 342/99 |
| 3,815,114 A | * | 6/1974 | Johnson et al. | 422/95 |
| 4,327,437 A | * | 4/1982 | Frosch et al. | 714/3 |
| 5,255,656 A | * | 10/1993 | Rader et al. | 123/494 |
| 5,731,510 A | * | 3/1998 | Jones et al. | 73/23.31 |
| 6,115,654 A | * | 9/2000 | Eid et al. | 701/34 |
| 2004/0238378 A1 | * | 12/2004 | Kumazawa et al. | 205/781 |
| 2005/0189238 A1 | * | 9/2005 | Howard et al. | 205/775 |
| 2006/0048036 A1 | * | 3/2006 | Miura et al. | 714/758 |

FOREIGN PATENT DOCUMENTS

| | | |
|---|---|---|
| JP | 7-21486 A | 1/1995 |
| JP | 2000-28139 A | 1/2000 |
| JP | 2004-061244 A | 2/2004 |
| JP | 2004061244 A * | 2/2004 |

OTHER PUBLICATIONS

English translation for JP 2004-061244.*
Abe et al., 2004-061244 (machine translated).*
Giles, Chapter 5, "Multiplexing: Sharing a Medium" (2003), Pennsylvania State University.*

* cited by examiner

*Primary Examiner* — Drew A Dunn
*Assistant Examiner* — Hyun Park
(74) *Attorney, Agent, or Firm* — Westerman, Hattori, Daniels & Adrian, LLP

(57) ABSTRACT

A gas sensor which includes: a plurality of gas detectors, each detects a target gas; an error detector which detects the occurrence of an error on each of gas sensors; an output selector which selects one output from among outputs entered from each gas sensor, the output selected by the output selector is the output from the gas detector in which no error exists; and an output unit which generate a normal output based on the output selected by the output selector and outputs the normal output to an external electrical device through a single output system, the output unit generates an abnormal output based on the output from the gas detector, in which the error exists, when the gas detector, in which an error exists, is detected, and outputs alternately the normal output and the abnormal output.

9 Claims, 7 Drawing Sheets

FIG. 4
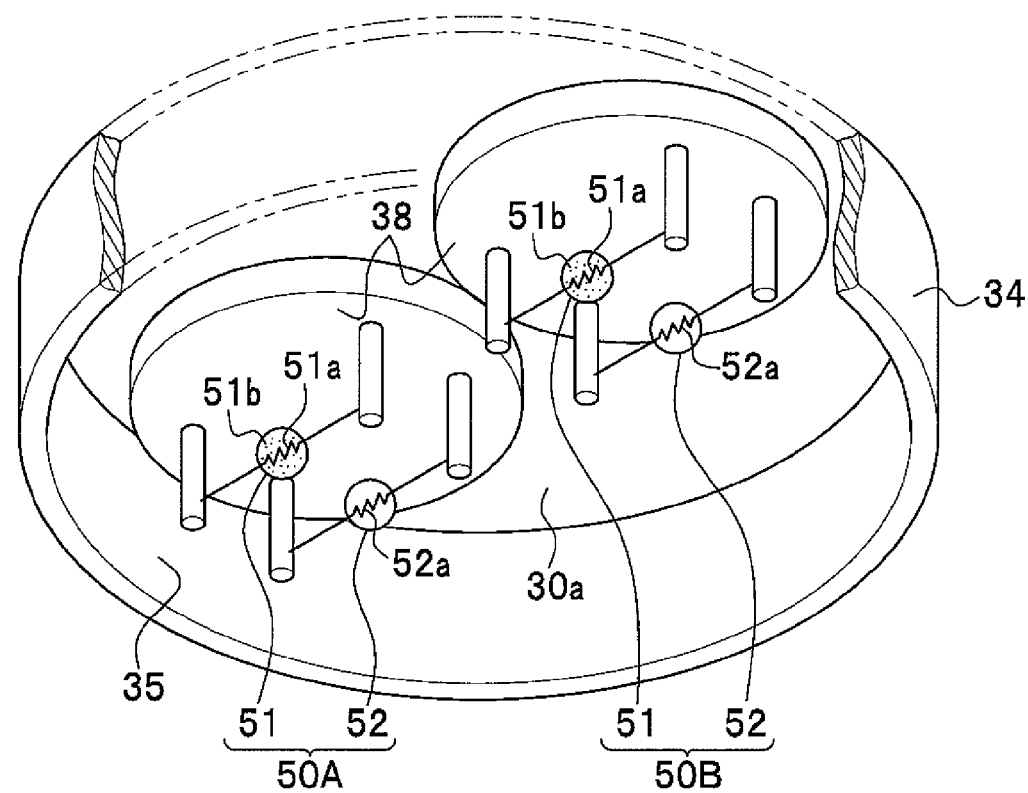
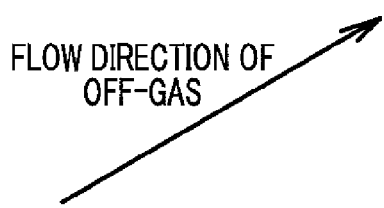

GAS SENSOR AND OUTPUT PROCESSING METHOD THEREOF

BACKGROUND OF THE INVENTION

1. Field of the Invention

The present invention relates to a gas sensor which connects with an external electric device, i.e. ECU (Electronic Control Unit), through a single output system. Also, the present invention relates to an output processing method to be performed on the gas sensor.

2. Description of Relevant Art

Generally, in a fuel cell which adopts solid polymer electrolyte membrane, a fuel cell stack is configured by stacking a plurality of single cells; each single cell is obtained by sandwiching a solid polymer electrolyte membrane by a fuel electrode and an oxygen electrode.

In this fuel cell, hydrogen is supplied, as fuel, to the fuel electrode and air is supplied, as oxidant, to the oxygen electrode. Then, hydrogen ion caused by a catalytic reaction at the fuel electrode passes through the solid polymer electrolyte membrane and reaches to the oxygen electrode. Thus, electric power is generated through an electrochemical reaction between hydrogen ion and oxygen.

In this kind of fuel cell adopting a solid polymer membrane, conventionally, a gas sensor is provided at an exhaust line of oxygen electrode-side, and a technique, which detects the leakage into the oxygen electrode side of hydrogen through the solid polymer membrane from the fuel electrode side using this sensor, has been discovered (see Japanese unexamined patent publication No. 2004-61244).

In the gas sensor disclosed in this Japanese unexamined patent publication, the gas sensor connects with ECU using two output systems, and supplies the outputs to ECU using two output systems. Here, one of outputs is the output based on a hydrogen concentration and the other of output is the output based on the error of the gas detector.

Therefore, the gas sensor, which connects with an external electric device through a single system and which can supply, by using this single system, the output which is determined based on a target gas and the output which is determined based on the error of the gas detector installed in the gas sensor, has been required.

SUMMARY OF THE INVENTION

The present invention relates to a gas sensor which includes: a plurality of gas detectors, each detects a target gas; an error detector which detects the occurrence of an error on each of gas sensors; an output selector which selects one output from among outputs entered from each gas sensor; and an output unit which generate a normal output based on the output selected by the output selector and outputs the normal output to an external electrical device through a single output system.

In this gas sensor, the output selected by the output selector is the output from the gas detector in which no error exists; and when the gas detector, in which an error exists, is detected, the output unit generates an abnormal output based on the output from the gas detector, in which the error exists, and outputs alternately the normal output and the abnormal output.

According to this gas sensor, the output unit outputs alternately the normal output and abnormal output; the abnormal output is generated based on the output (e.g. level of error on the gas detector and etc) supplied from the gas detector in which error exists; and the abnormal output is generated based on the output (e.g. an gas concentration of the target gas and etc) supplied from the gas detector in which no error exists.

In other words, the output unit intermittently outputs the abnormal output instead of normal output during the continuous output of the normal output.

Thereby the external electrical device, which connects with a single output system, can detect the normal output and the abnormal putout.

In this invention, it is preferable that the output unit do not output the abnormal output when normal output satisfies a predetermined requirement.

According to this gas sensor, the output unit does not output the abnormal output, when normal output supplied from the gas detector in which no error exists satisfies a predetermined requirement. In this case, the output of the normal output is prioritized over the output of the abnormal output. Here, the term "normal output supplied from the gas detector in which no error exists satisfies a predetermined requirement" denotes that the hydrogen concentration detected by the reference detector (gas detector) exceeds a predetermined hydrogen concentration.

In this invention, it is preferable that the output unit adjusts the interval of the output of the abnormal output based on the level of the error on the gas detector, in which an error exists.

According to this gas sensor, the detection of the occurrence of the error by the external electric device is surely achieved, by adjusting the interval of the output of the abnormal output.

In this invention, it is preferable that the output unit adjusts the intensity of the output of the abnormal output based on the level of the error on the gas detector, in which the error exists.

According to this gas sensor, the detection of the occurrence of the error by the external electric device is surely achieved, by adjusting the intensity of the output of the abnormal output.

The present invention relates to an output processing method to be performed on a gas sensor having a plurality of gas detectors which detect a target gas for processing an output based on the target gas and an output based on the gas sensor. This method includes the steps of: detecting an occurrence of an error on each of gas sensors by an error detector; selecting, based on the detection result of the error detector, one output from among outputs entered from each gas sensor; and outputting an normal output, which is generated based on the output selected by the output selector, to an external electrical device through a single output system. In this method, the output selected by the output selector is the output from the gas detector in which no error exists, the output unit generates an abnormal output based on the output from the gas detector, in which the error exists, when the gas detector, in which an error exists, is detected, and the output unit outputs alternately the normal output and the abnormal output.

According to the present invention, the gas sensor, which connects with an external electric device through a single system and which can supply, by using this single system, the output which is determined based on a target gas and the output which is determined based on the error of the gas detector installed in the gas sensor, can be presented.

BRIEF DESCRIPTION OF THE DRAWINGS

FIG. 4 is a perspective view of the gas detector.

DETAILED DESCRIPTION OF THE PREFERRED EMBODIMENT

The preferred embodiments of the present invention will be explained with reference to the attached drawings.

<<Fuel Cell System>>

Figure 1:
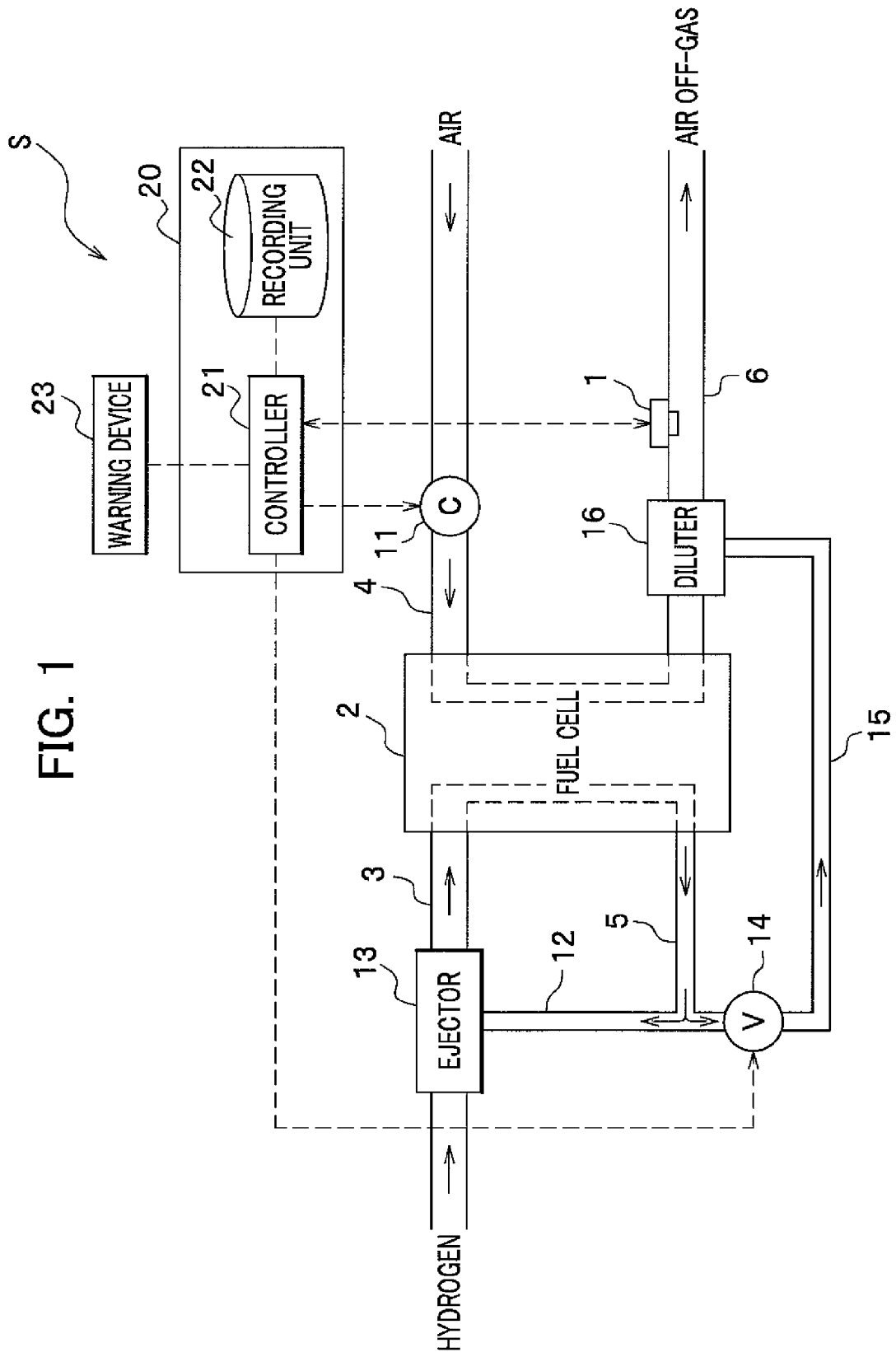
FIG. 1 is a block diagram indicating the configuration of the fuel cell system according to the present embodiment.

As shown in FIG. 1, a fuel cell system S according to the present embodiment is a system installed on a fuel-cell-powered vehicle (vehicle). In this fuel-cell-powered vehicle, a drive motor (not shown) is driven by a power from a fuel cell 2 for driving a vehicle.

The fuel cell system S mainly includes the fuel cell 2, an anode side inlet line 3, an anode side outlet line 5, a cathode side inlet line 4, a cathode side outlet line 6, ECU 20, and a hydrogen sensor 1. Here, the fuel cell 2 serves as a power source; the anode side inlet line 3 (inlet line 3) and the anode side outlet line 5 (outlet line 5) are the piping disposed at the fuel electrode side of the fuel cell 2; the cathode side inlet line 3 (inlet line 3) and the cathode side outlet line 6 (outlet line 6) are the piping disposed at the oxygen electrode side of the fuel cell 2; the ECU 20 controls the fuel cell system S as a whole; and the hydrogen sensor 1 (gas sensor) is disposed on the outlet line 6 and detects a hydrogen (target gas).

The fuel cell 2 is formed by stacking one by one a plurality of single cells (not shown). Here, each single cell is obtained by sandwiching membrane electrode assemblies (MEAs) by a pair of separators, and the membrane electrode assemblies (MEAs) is obtained by sandwiching a solid polymer electrolyte membrane, e.g. a cation-exchange membrane, by the fuel electrode and the oxygen electrode.

To this fuel cell 2, hydrogen, which serves as a fuel, is supplied through the inlet line 3 from a hydrogen supply unit (not shown) equipped with a high pressure hydrogen tank, and air, which serves as an oxidant, is supplied through the inlet line 4 by a compressor 11.

Then, hydrogen is ionized by a catalytic reaction on a catalytic electrode of the fuel electrode, and causes a hydrogen ion. The hydrogen ion caused by a catalytic reaction passes through the solid polymer electrolyte membrane, which has been humidified appropriately, and reaches to the oxygen electrode.

During this transfer of the hydrogen ion within fuel cell, electron passes through an external circuit including the driven motor and is used for the generation of DC electric energy (power).

Here, since air containing oxygen is supplied to the oxygen electrode, water is caused by an electrical reaction between hydrogen ion, electron, and air, under the action of the catalyst of the oxygen electrode. In this embodiment, the compressor 11 is driven under the control of ECU 20 based on a command signal which commands the electric generation. Then, an off-gas including unreacted gas, e.g. hydrogen, oxygen, and etc., is discharged through the outlet line 5 and the outlet line 6.

Here, a hydrogen off-gas (anode off-gas) containing unreacted hydrogen is discharged through the outlet line 5 of the fuel electrode side to a circulation pipeline 12 and is then returned to the inlet line 3 through an ejector 13. Thereby, hydrogen contained in off-gas is again supplied to the fuel electrode of the fuel cell 2. An air off-gas (cathode off-gas), i.e. an air containing excessive amount of moisture, is ejected into atmosphere through a diluter 16 and the outlet line 6.

Additionally, one end of a hydrogen exhaust line 15 connects with the outlet line 5 through a purge valve 14 and the other end of the hydrogen exhaust line 15 connects with the diluter 16. The hydrogen off-gas is allowed to be supplied into the hydrogen exhaust line 15 through the purge valve 14, and is also allowed to be supplied to the diluter 16 through the hydrogen exhaust line 15.

The hydrogen off-gas supplied through the hydrogen exhaust line 15 is diluted, by the diluter 16, with the air off-gas supplied through the outlet line 6 at a predetermined dilution rate, and is discharged as a dilution gas. In this embodiment, the opening-and-closing of the purge valve 14 is controlled by ECU 20.

A hydrogen sensor 1, which is a catalytic combustion sensor for detecting hydrogen, is provided on the outlet line 6. The position where the hydrogen sensor 1 is provided is downstream of the diluter 16. Thereby, the checking of the hydrogen concentration in the off-gas, i.e. an air off-gas and a dilution gas, is enabled.

The hydrogen sensor 1 is disposed on the outlet line 6, which is disposed so that the flow direction of gas is a horizontal direction. Here, the position where the hydrogen sensor 1 is disposed is at the upper portion in a vertical direction of the outlet line 6. Also, the hydrogen sensor 1 electrically connects with a controller 21 of ECU (electric control unit: electric controller) 20 which controls the operation of the fuel cell system S via a single output system (so called as 1-pin).

ECU 20 includes CUP, ROM, RAM, various interfaces, and electric circuit etc., and has the controller 21 and a recording unit 22. The controller 21 electrically connects with a compressor 11 and the purge valve 14, and controls the operation of these components as appropriate.

The controller 21 electrically connects with the hydrogen sensor 1 through a single output system. Also, the controller 21 computes a hydrogen concentration based on an output (normal output), which is supplied from the hydrogen sensor 1 and is determined in accordance with the hydrogen concentration, and a hydrogen concentration map stored in the recording unit 22. Then, the controller 21 outputs the computed hydrogen concentration to a monitor (not shown) which is used for indicating the computed hydrogen concentration. Here, the hydrogen concentration map is a data indicating the correlation between the normal output supplied from the hydrogen sensor 1 and the hydrogen concentration.

The controller 21 additionally determines what types of error has occurred on the hydrogen sensor 1 based on an output (abnormal output) supplied from the hydrogen sensor 1 and an abnormal output map stored in the recording unit 22. The controller 21 turns on a warning device 23, e.g. a warning light, when an error exists in the hydrogen sensor 1. Here, the abnormal output map is a data indicating the correlation between the abnormal output supplied from the hydrogen sensor 1 and the level of the abnormal of the hydrogen sensor 1.

<Configuration of Hydrogen Sensor>

The hydrogen sensor 1 detects hydrogen within off-gas, i.e. air off-gas and a dilution gas, which is flowing through the outlet-line 6. Then, the hydrogen sensor 1 outputs a signal (output signal), which is determined in accordance with the concentration of the detected hydrogen, to the controller 21 of ECU 20. The hydrogen sensor 1 has a function (a self error check function) to check the occurrence of an error on a reference detector 50A and regular detector 50B, and outputs a signal (error output) which is determined in accordance with the detected error, when the occurrence of error is detected.

<Mechanical Configuration of Hydrogen Sensor>

Next, mechanical configuration of the hydrogen sensor 1 will be explained with reference to FIG. 2 to FIG. 4.

Figure 2:
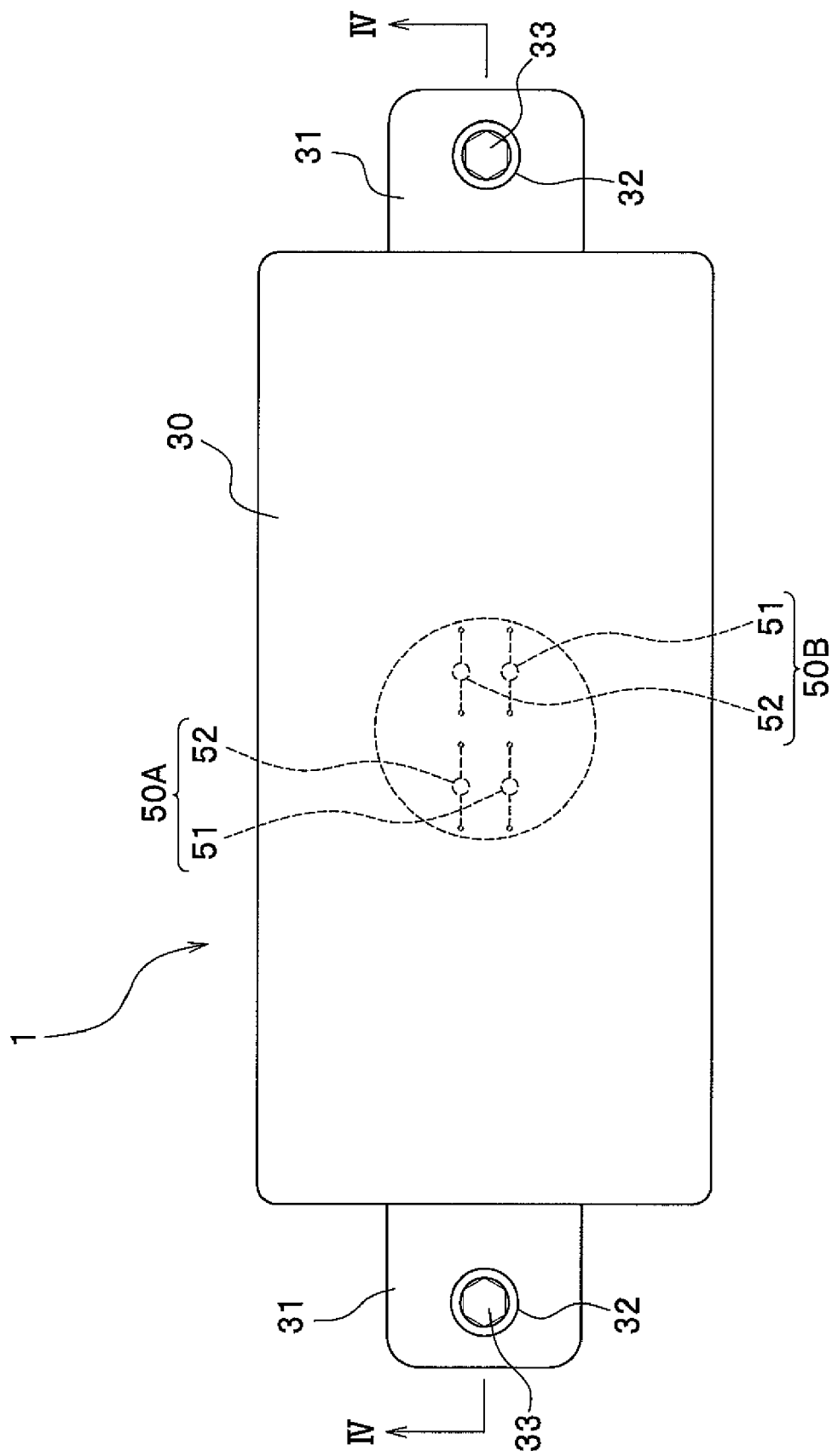
FIG. 2 is a plane view showing the hydrogen sensor.
Figure 3:
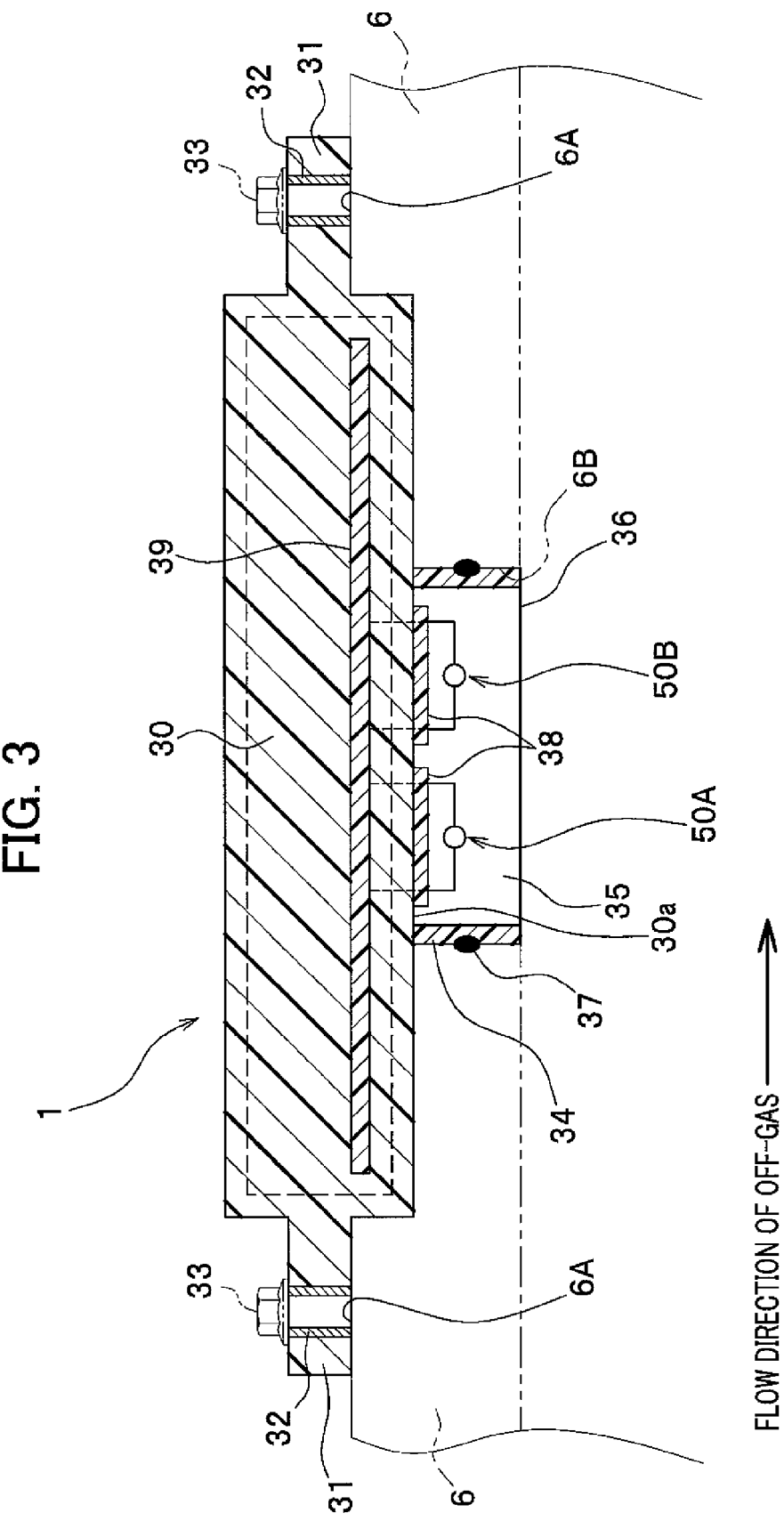
FIG. 3 is a IV-IV sectional view of the hydrogen sensor of FIG. 2.

As shown in FIG. 2 and FIG. 3, the hydrogen sensor 1 includes a case 30 which has a rectangular parallelepiped shape and accommodates therein a control board 39. The case 30 is, for example, made of polyphenylene sulfide, and has a flange 31 at both ends in a longitudinal direction of the case 30. A collar 32 is provided to each flange 31, and by inserting a bolt 33 into this collar 32, the flange 31 is fixed to a mount 6A (see FIG. 3) which is disposed on the outlet line 6.

As shown in FIG. 3, a cylindrical section 34 is formed at an underside surface 30a in a thickness direction of the case 30. The tip of the cylindrical section 34 is opened to take therein the off-gas containing hydrogen and serves as a gas intake 36. The inside of the cylindrical section 34 serves as a gas detection chamber 35, and the reference detector 50A (gas detector) and the regular detector 50B (gas detector) are respectively disposed on the underside surface 30a through bases 38 and 38. That is, the reference detector 50A and the regular detector 50B are serves as two (plural) gas detectors of the hydrogen sensor 1.

A sealing member 37 is disposed along an outer periphery of the cylindrical section 34. The hydrogen sensor 1 is attached to the outlet line 6 by inserting the cylindrical section 34 into a through hole 6B formed on the outlet line 6. The sealing member 37 contacts, to keep an air tight, with the inner periphery of the through hole 6B and the outside periphery of the cylindrical section 34.

Next, the reference detector 50A and the regular detector 50B which serve as a gas detector will be explained in detail.

As shown in FIG. 4, the reference detector 50A and the regular detector 50B are respectively comprised of a pair of a detection element 51 and a thermal compensation element 52. The detection element 51 is a well-know element and is obtained by covering a coil 51a which is formed from a metal wire using a carrier, e.g. alumina, which holds therein a catalyst 51b. In this embodiment, a metal wire, which includes a metal, e.g. platinum etc., whose temperature coefficient against electric resistance is high, is adopted for forming the coil 51a. The catalyst 51b is made of noble metal which is active against a target gas, e.g. hydrogen etc.

The thermal compensation element 52 is inactive against a target gas, and is, for example, obtained by covering the surface of the coil 52a, which is almost equivalent to the detection element 51, by a carrier, e.g. alumina etc.

When the target gas contacts with the catalyst 51b, the temperature of the detection element 51 becomes high due to a reaction heat caused by a catalytic reaction between the target gas and the catalyst 51b. In this case, since the difference between the resistance value of the detection element 51 and the resistance value of the thermal compensation element 52 arises, the concentration of hydrogen can be measured based on this difference. In this embodiment, the influence of the change in the resistance value that is caused depending on an ambient temperature can be cancelled by using the thermal compensation element 52.

The detection element 51 is disposed in the vicinity of the thermal compensation element 52, and the reference detector 50A is also disposed in the vicinity of the regular detector 50B.

In this embodiment, the detection element 51 and the thermal compensation element 52 are disposed separating a predetermined distance from the base 38, and the distance from base 38 to detection element 51 is the same as the distance from the base 38 to the thermal compensation element 52.

Here, the term of "vicinity" means that each element is within the area in which ambient atmosphere is the same. In this case, for example, each element is within the area in which the concentration and temperature of hydrogen (target gas) is approximately the same.

As for the hydrogen concentration measured by the reference detector 50A and regular detector 50B, each element is disposed so that the deviation between values from the reference detector 50A and the regular detector 50B is within a predetermined range, e.g. within the range of ±20%. In this embodiment, it is more preferable that the deviation is within the range of ±10%, and also it is still more preferable that the deviation is within a range of ±5%.

<Electrical Configuration of Hydrogen Sensor>

Next, the electrical configuration of the hydrogen sensor 1 including the control board 39 will be explained with reference to FIG. 5.

Figure 5:
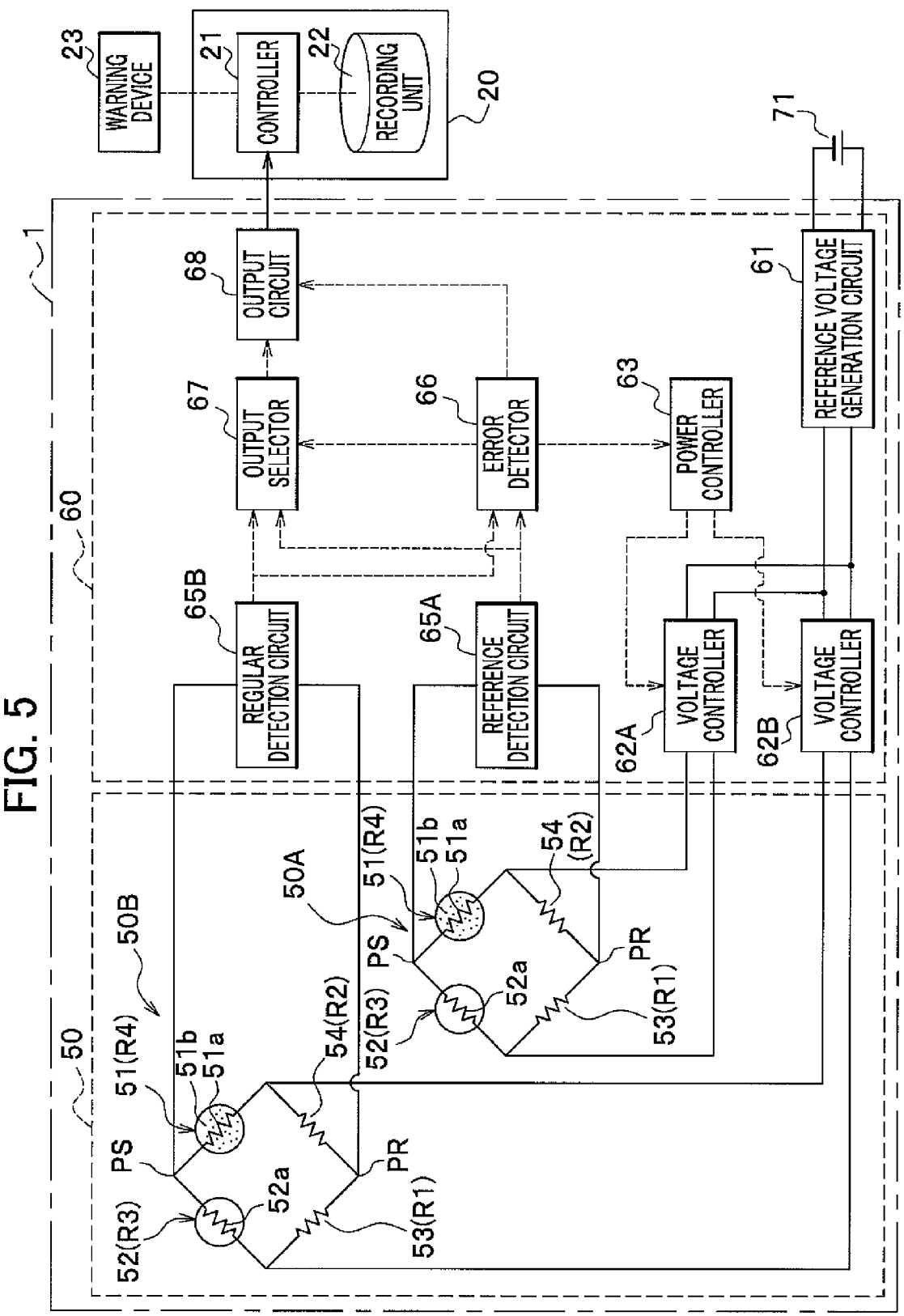
FIG. 5 is a block diagram showing the configuration of the detection unit and circuit unit of the hydrogen sensor according to the present embodiment.

As shown in FIG. 5, the hydrogen sensor 1 includes a detection unit 50 and a circuit unit 60. Here, the detection unit 50 includes the reference detector 50A and the regular detector 50B, and the circuit unit 60 performs the processing of the output from detection unit 50 and outputs the processing result to the controller 21 of ECU 20.

In each of the reference detector 50A and the regular detector 50B, a first line, in which detection element 51 (resistance value: R4) and the thermal compensation element 52 (resistance value: R3) are serially connected, and a second line, in which a fixed resistance 53 (resistance value: R1) and a fixed resistance 54 (resistance value: R2) are serially connected, are connected in parallel to a reference voltage generation circuit 61 of the circuit unit 60 which applies a predetermined reference voltage. That is, each of reference detector 50A and regular detector 50B configures a bridged circuit. Here, the connection between the first line and the second line is controlled based on a voltage supplied from an external power source 71 (secondary battery) of the hydrogen sensor 1.

In this embodiment, as for the bridge circuit of the reference detector 50A, a reference detection circuit 65A connects with a connection point PS and a connection point PR to measure the voltage between the connection point PS and the connection point PR. Also, as for the bridge circuit of the regular detector 50B, a regular detection circuit 65B connects with a connection point PS and a connection point PR to measure the voltage between the connection point PS and the connection point PR. Here, the connection point PS is the connection point between the detection element 51 and the thermal compensation element 52, and the connection point PR is the connection point between the fixed resistance 53 and the fixed resistance 54.

When no hydrogen (target gas) exists in the gas introduced into the gas detection chamber 35 (see FIG. 3), each bridged circuit is balanced and satisfies the following relation: R1×R4=R2×R3. In this case, the output from each of the reference detection circuit 65A and the regular detection circuit 65B is zero.

When hydrogen (target gas) exists in the gas, the temperature of the coil 51a rises due to the hydrogen combustion at the catalyst 51b of the detection element 51, and thereby the resistance value R4 increases. In the thermal compensation element 52, on the other hand, since the combustion of hydrogen is not caused, the resistance value R3 is unchanged (constant). Thereby, since the balance in the bridged circuits is disrupted, a voltage in accordance with the change of the concentration of hydrogen is applied to the reference detection circuit 65A and the regular detection circuit 65B from the reference detector 50A and the regular detector 50B, respectively.

Each of the reference detection circuit 65A and the regular detection circuit 65B outputs the value of the voltage of the bridged circuit to each of an error detector 66 and output selector 67 as a detected value (output).

<Error Detector>

Figure 6:
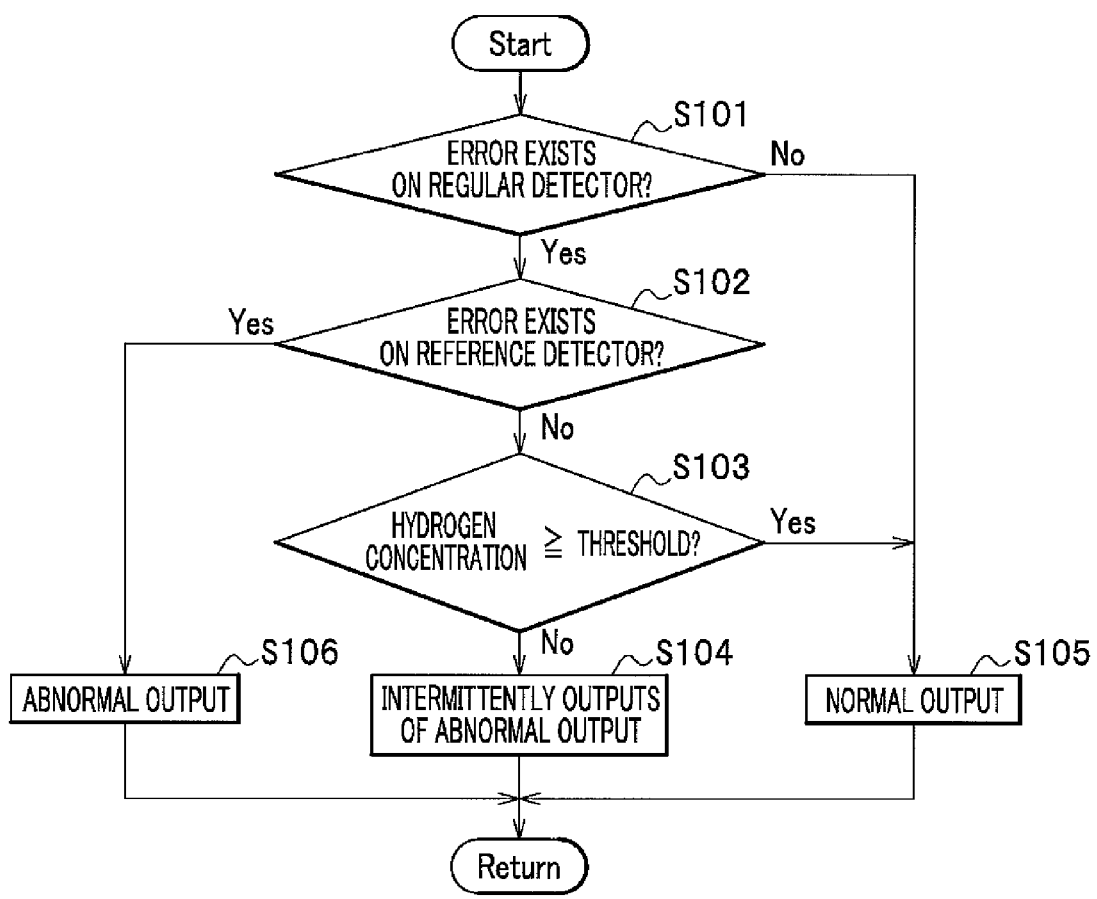
FIG. 6 is a flow chart for explaining the processing of the hydrogen sensor according to the present embodiment.

The error detector 66 (error detection unit) performs an absolute diagnosis in order to check whether or not an error, e.g. the occurrence of a deterioration on each detection element, has arisen in the reference detection circuit 65A and the regular detection circuit 65B (FIG. 6, S101 and S102). To be more precise, the error detector 66 compares each of the detected value (output) of the reference detection circuit 65A and the detected value (output) of the regular detection circuit 65B with a predetermined reference value which is stored in the error detector 66. Then, the error detector 66 outputs the result (judgment result) of the comparison to the output selector 67 and an output circuit 68.

In this embodiment, it is judged that an error is caused on the reference detection circuit 65A (the regular detection circuit 65B), when for example the difference between the detected value and the predetermined reference value exceeds a threshold value. In this case, it is expected that deterioration or short circulation has arisen on the reference detector 50A (the regular detector 50B).

On the other hand, it is judged that an error is not caused on the reference detection circuit 65A (the regular detection circuit 65B), when for example the difference between the detected value and the predetermined reference value does not exceed a threshold value. In this case it is expected that the reference detector 50A (the regular detector 50B) works properly.

Hereinafter, the term "abnormal condition" is used for indicating that an error exists as appropriate, the term "normal condition" is used for indicating that an error does not exist as appropriate. That is, "the reference detection circuit 65A is in an abnormal condition" denotes that an error exists on the reference detection circuit 65A.

<Output Selector>

The output selector 67 selects, in accordance with the judgment result entered from the error detector 66, the detected value entered from the reference detection circuit 65A (reference detector 50A) or the detected value entered from the regular detection circuit 65B (regular detector 50B). Then, the output selector 67 outputs the selected detected value, as detected value, to the output circuit 68.

To be more precise, (1) the output selector 67 selects the detected value entered from the regular detection circuit 65B, when the judgment result, which indicates no error exists on both of the reference detector 50A and the regular detector 50B, is entered. Then, the output selector 67 outputs the selected detected value to the output circuit 68.

(2) the output selector 67 selects the detected value entered from the reference detection circuit 65A, when the judgment result, which indicates error exists only on the regular detector 50B, is entered. Then, the output selector 67 outputs the selected detected value to the output circuit 68. On the contrary, the output selector 67 selects the detected value entered from the regular detection circuit 65B, when the judgment result, which indicates error exists only on the reference detector 50A, is entered. Then, the output selector 67 outputs the selected detected value to the output circuit 68.

(3) Furthermore, the output selector 67 does not select any of the detected signal entered from the reference detection circuit 65A and the detected signal entered from the regular detection circuit 65B, when the judgment result, which indicates that an error exists on both of the reference detection circuit 65A and the regular detection circuit 65B, is entered from the error detector 66. In this case, no output is entered to the output circuit 68.

<Output Circuit>

The output circuit 68 is a circuit which outputs "normal output" and "error output" to the controller 21 of ECU 20. Here, the meaning of "normal output" and "error output" will be explained later in detail.

To be more precise, (1) the output circuit 68 generates a signal (normal output) based on the detected value entered from the output selector 67, when the judgment result, which indicates that no error exists on both of the reference detector 50A and the regular detector 50B, is entered from the error detector 66. Then, the output circuit 68 outputs the generated signal (normal output) to the controller 21.

Also, (2) the output circuit 68 generates a signal (normal output) based on the detected value entered from the detector in which no error exists, and a signal (abnormal output) based on the detected value entered from the detector in which an error exists, when the judgment result, which indicates that an error exists on one of the reference detector 50A and the regular detector 50B, is entered from the error detector 66.

That is, when the judgment result indicates that the reference detector 50A is in the normal condition and the regular detector 50B is in the abnormal condition, the output circuit 68 generates the normal output based on the detected value entered from the reference detector 50A and the abnormal output based on the detected value entered from the regular detector 50B.

Figure 7:
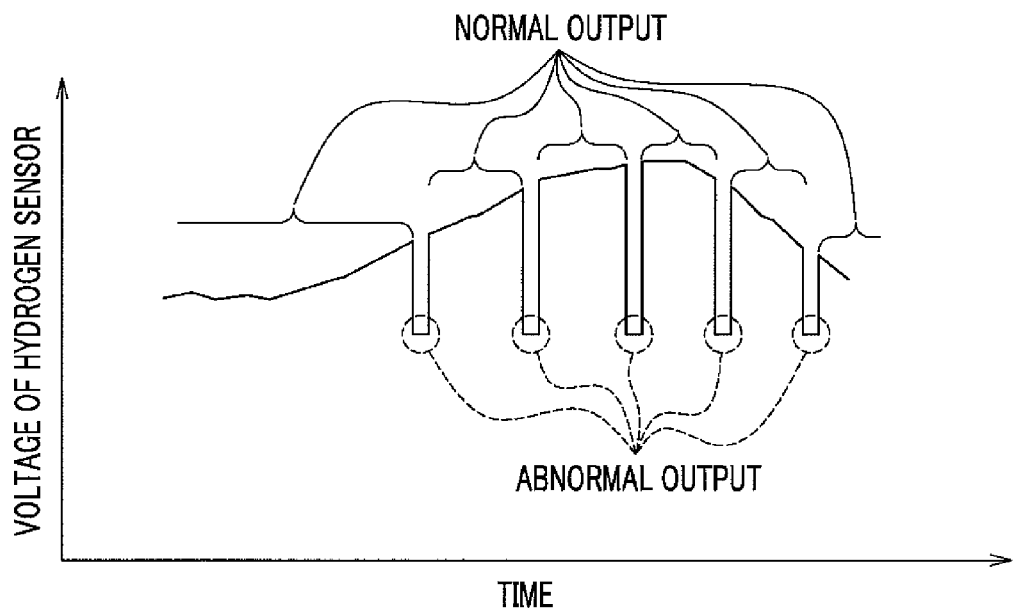
FIG. 7 is a graph indicating the output of the hydrogen sensor according to the present embodiment.

Then, the output circuit 68 outputs alternately the normal output and the abnormal output. To be more precise, as shown in FIG. 7, for example, the output circuit 68 intermittently outputs the abnormal output instead of normal output during the continuous output of the normal output corresponding to the detected hydrogen concentration.

Here, the range of the abnormal output to be supplied from the output circuit 68 is established at the outside of the range to be used for the value of the normal output to prevent the occurrence of the detection error of the controller 21.

In this embodiment, additionally, the interval of the output of abnormal output may be changed (adjusted) in accordance with the level of the abnormal condition of the detector (reference detector 50A or regular detector 50B) in which error exists. In this embodiment, still furthermore, the value of the abnormal output may be changed (adjusted) in accordance with the level of the abnormal condition of the detector (reference detector 50A or regular detector 50B) in which error exists. By changing (adjusting) the level and the interval of the output of the abnormal output, the occurrence of the detection error on the controller 21 can be decreased.

(3) Furthermore, the output circuit 68 generates a signal (abnormal output) when the judgment result, which indicates that an error exists on both of the reference detection circuit 65A and the regular detection circuit 65B, is entered from the error detector 66. Then, the output circuit 68 outputs the abnormal output to the controller 21. Here, as described above, there is no input from the output selector 67, when both of the reference detector 50A and the regular detector 50B are in the abnormal condition. Thus, the abnormal output does not include the data relating to the hydrogen concentration.

<Voltage Controller and Power Controller>

A voltage controller 62A is provided between the reference detector 50A and a reference voltage generation circuit 61. A power controller 63 supplies a command, which commands a voltage controller 61A to control the voltage to be applied to the reference detector 50A, to the voltage controller 62A. Thereby, the voltage controller 62A controls the voltage to be applied to the reference detector 50A in accordance with the command.

A voltage controller 62B is provided between the regular detector 50B and the reference voltage generation circuit 61. The power controller 63 supplies a command, which commands the voltage controller 62B to control the voltage to be applied to the regular detector 50B, to the voltage controller 62B. Thereby, the voltage controller 62B controls the voltage to be applied to the regular detector 50B in accordance with the command.

In this embodiment, the power controller 63 controls the motion of each of the voltage controllers 62A and 62B by using a command, in accordance with the judgment result entered from the error detector 66 or in accordance with a predetermined timing.

<Motion of Hydrogen Sensor>

Figure 8:
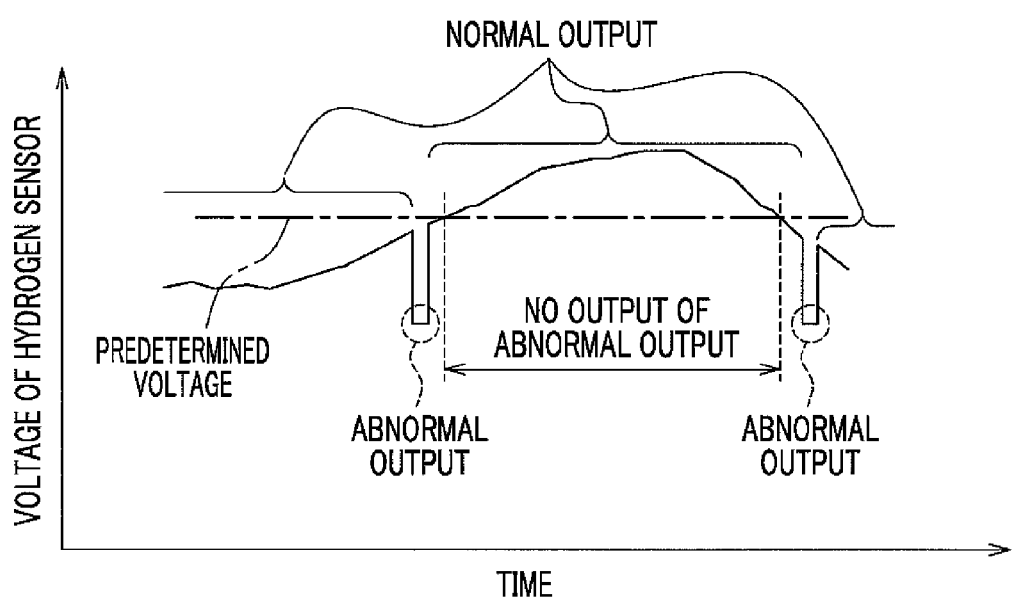
FIG. 8 is a graph indicating the output of the hydrogen sensor according to the present embodiment.

Next, the motion of the hydrogen sensor 1 according to the present embodiment will be explained with reference to FIG. 6 to FIG. 8.

Firstly, the hydrogen sensor 1 is turned on in conjunction with the turn on of an ignition switch of a fuel cell vehicle. Then, the processing shown in the flowchart of FIG. 6 is started and the processing proceeds to step S101.

In step S101, the error detector 66 checks whether or not the regular detector 50B is in abnormal condition. When it is judged that the regular detector 50B is in abnormal condition (step S101, Yes), the processing proceeds to step S102.

When it is judged that the regular detector 50B is in normal condition (step S101, No), the error detector 66 outputs the judgment result, which indicates that the regular detector 50B is in normal condition, to the output selector 67 and the output circuit 68. Thereby, the output selector 67 selects the detected value entered from the regular detection circuit 65B (regular detector 50B), and outputs it to the output circuit 68.

Then, the output circuit 68 generates a signal (normal output) based on the detected value entered from the output selector 67, and outputs this normal output, as standard output, to the controller 21 (step S105). After this, the processing proceeds to "RETURN" and backs to "START". Thereby, the controller 21 can detect the hydrogen concentration based on this normal output.

In step S102, the error detector 66 checks whether or not the reference detector 50A is in abnormal condition. When it is judged that the reference detector 50A is in abnormal condition (step S102, Yes), the processing proceeds to step S106.

In step S106, the error detector 66 outputs the judgment result, which indicates that the reference detector 50A and the regular detector 50B are in abnormal condition, to the output selector 67 and the output circuit 68.

Thereby, the output selector 67 does not select any output value supplied from reference detection circuit 65A and regular detection circuit 65B, and thus no output is supplied to the output circuit 68 from the output selector 67.

In this case, the output circuit 68 outputs the abnormal output, which indicates that the detector 50A and the regular detector 50B are in abnormal condition, to the controller 21. After this, the processing proceeds to "RETURN". Here, when only abnormal output is entered to the controller 21, the controller 21 judges that there is an error on the reference detector 50A and regular detector 50B, and turns on the warning device 23.

When it is judged that the reference detector 50A is in normal condition (step S102, No), the error detector 66 outputs the judgment result, which indicates that the reference detector 50A is in normal condition and the regular detector 50B is in abnormal condition, to the output selector 67 and the output circuit 68. Thereby, the output selector 67 selects the detected value from the reference detection circuit 65A (reference detector 50A) and outputs it to the output circuit 68. Then, the processing proceeds to step S103.

In step S103, the output circuit 68 compares the input value entered from the output selector 67 with the predetermined voltage (threshold value), which has been established beforehand in accordance with the hydrogen concentration, and checks whether or not the hydrogen concentration measured by the reference detector 50A exceeds the predetermined hydrogen concentration. Here, in this embodiment, the predetermined voltage changes according to the concentration of hydrogen.

When it is judged that the hydrogen concentration measured by the reference detector 50A exceeds the predetermined hydrogen concentration (step S103, Yes), the processing proceeds to step S105. The output circuit 68 does not output the abnormal output which indicates that the regular detector 50B is in abnormal condition. The output circuit 68 selects the output, which was supplied from the reference detector 50A through the reference detection circuit 65A, and outputs the selected output to the controller 21 (see FIG. 8).

In this embodiment, the output circuit 68 prioritizes the output, which indicates whether or not hydrogen exceeds the predetermined concentration, over the output, which indicates the condition of the regular detector 50B. That is, the fundamental function of the hydrogen sensor 1, i.e. the checking of whether or not hydrogen more than the predetermined concentration is detected, is prioritized.

When it is judged that the hydrogen concentration measured by the reference detector 50A does not exceed the predetermined hydrogen concentration (step S103, No), on the other hand, the processing proceeds to step S104. Then, as shown in FIG. 7, the output circuit 68 alternately outputs a normal output and an abnormal output when the judgment result, which indicates that the reference detector 50A is in the normal condition and the regular detector 50B is in the abnormal condition, is entered from the error detector 66. In this case, the normal output is an output based on the reference detector 50A and the abnormal output is an output based on the error condition of the regular detector 50B.

That is, the output circuit 68 intermittently outputs an abnormal output indicating that an error exists on the regular detector 50B, instead of normal output during the continuous output of the normal output. Here, in this embodiment, the hydrogen concentration which was detected by the reference detector 50A can be recognized based on normal output.

Thereby, based on the normal output from the reference detector 50A, the controller 21 computes the hydrogen concentration in the off-gas, which is passing through the outlet line 6. Then, the controller 21 turns on the warning device 23 when it is required (e.g. when hydrogen concentration exceeds a threshold value).

That is, ECU 20 can detect the hydrogen concentration measured by the hydrogen sensor 1 and recognize the occurrence of the error on the hydrogen sensor 1, even if the ECU 20 and the controller 21 are connected each other through a single output system.

Here, the interval of the output of the abnormal output which indicates the occurrence of the error on the regular detector 50B may be changed in accordance with the level of the error on the regular detector 50B. Additionally, the intensity of the abnormal output may be changed in accordance with the level of the error.

Although there have been disclosed what are the patent embodiment of the invention, it will be understood by person skilled in the art that variations and modifications may be made thereto without departing from the scope of the invention, which is indicated by the appended claims.

In the above described embodiment, the explanation has been made on assumption that the target gas is hydrogen. However, target gas is not limited to hydrogen, and other kinds of gas, e.g. carbon monoxide, hydrogen sulfide, and etc., can be adoptable as the target gas. Additionally, in the above described embodiment, a catalytic combustion type gas-sensor is adopted as the gas sensor, but other types of sensor, e.g. a semiconductor type gas-sensor, can be adoptable.

In the above described embodiment, the hydrogen sensor 1 includes the reference detector 50A and the regular detector 50B as a plurality of gas detectors. The number of gas detector elements is not limited to the number of this embodiment. For example, the hydrogen sensor 1 can include a plurality of reference detectors 50A and regular detectors 50B.

In the above described embodiment, the error judgment (deterioration diagnosis) of the reference detector 50A and the regular detector 50B is performed by the error detector 66, by an absolute diagnosis, in which each of the detected value of the reference detector 50A and the regular detector 50B is separately compared with the predetermined reference value.

The judgment of the error is not limited to this method, for example, a relative judgment which compares relatively the detected value of the reference detector 50A with the detected value of the regular detector 50B can be adoptable instead of the absolute judgment.

In the above described embodiment, the hydrogen sensor 1 is disposed on the outlet lint 6 in which off-gas of the fuel cell system S passes through. The position of the hydrogen sensor is not limited to this. For example, in the case of the fuel-cell-powered vehicle, the hydrogen sensor may be disposed within the vehicle. Additionally, the hydrogen sensor may be disposed on the stationary fuel-cell system for home use.

In the above described embodiment, the reference detector 50A and the regular detector 50B are disposed along the longitudinal direction of the hydrogen sensor 1. But the position of the reference detector 50A and the regular detector 50B is not limited to this location. The position of the reference detector 50A and the regular detector 50B can be modified, as long as the reference detector 50A and the regular detector 50B are positioned close to each other and provide necessary functions. For example, the reference detector 50A and the regular detector 50B of each of the base 38 can be stacked in double.

What is claimed is:

1. A gas sensor comprising:
   a plurality of gas detectors, each of which detects a target gas and is a reference detector or a regular detector;
   an error detector to detect an occurrence of an error on each of the plurality of gas detectors and send a result of the occurrence of the error to both an output selector and an output unit;
   said output selector selects one output in which no error exists from among outputs sent from each of the plurality of gas detectors; and
   said output unit receives an output signal from said output selector and generates a normal output based on the output signal when no error exists and outputs the normal output to an external electrical device through a single output system,
   wherein said output unit is configured to generate an abnormal output when the output of the error detector indicates that an error exists on one of the plurality of gas detectors so as to output alternately the normal output received from said output selector and the abnormal output based on the output of the error detector to the external electrical device through said single output system,
   wherein the range of the abnormal output to be supplied from the output unit is set outside the range of the normal output, and
   wherein the output device has a normal output mode, an abnormal output mode, and an intermittent output mode,
   in the normal output mode, the output device outputs a signal detected by the regular detector if no error exists in both the reference detector and the regular detector, and the output device outputs a signal detected by the regular detector if an error exists in the regular detector and does not exist in the reference detector and if a concentration of hydrogen existing in the reference detector is greater than a predetermined concentration,
   in the abnormal output mode, the output device outputs a signal indicating that an error exists in both the reference detector and the regular detector,
   in the intermittent output mode, the output device outputs alternately the signal indicating that no error exists in the reference detector and the signal indicating that an error exists in the regular detector if the concentration of hydrogen existing in the reference detector is lower than the predetermined concentration.

2. A gas sensor according to claim 1, wherein
   the output unit does not output the abnormal output when normal output satisfies a predetermined requirement.

3. A gas sensor according to claim 1, wherein
   the output unit adjusts the interval of the output of the abnormal output based on the level of the error on said one of the gas detectors, in which the error exists.

4. A gas sensor according to claim 1, wherein
   the output unit adjusts the intensity of the output of the abnormal output based on the level of the error on said one of the gas detectors, in which the error exists.

5. A gas sensor according to claim 1, wherein
   the gas detector is a bridge circuit formed by connecting a first line, in which detection element and the thermal compensation element are serially connected, and a second line, in which a fixed resistance and a fixed resistance are serially connected,
   the detection element is active against the target gas and the thermal compensation element is inactive against the target gas.

6. An output processing method to be performed on a gas sensor having a plurality of gas detectors, each of which detects a target gas for processing an output based on the target gas and an output based on the gas sensor and is a reference detector or a regular detector, the method comprising the steps of:
   detecting an occurrence of an error on each of the plurality of gas detectors by an error detector;
   sending a result of the occurrence of the error to both an output selector and an output unit;

selecting, based on the detection result of the error detector, one output in which no error exists from among outputs sent from each of the plurality of gas detectors; and outputting a normal output, which is generated based on an output signal received from said output selector in which no error exists, to an external electrical device through a single output system, wherein said output unit is configured to generate an abnormal output when the output of the error detector indicates that an error exists on one of the plurality of gas detectors so as to output alternately the normal output received from said output selector and the abnormal output based on the output of the error detector to the external electrical device through said single output system, wherein the range of the abnormal output to be supplied from the output unit is set outside the range of the normal output, and wherein the output device has a normal output mode, an abnormal output mode, and an intermittent output mode, in the normal output mode, the output device outputs a signal detected by the regular detector if no error exists in both the reference detector and the regular detector, and the output device outputs a signal detected by the regular detector if an error exists in the regular detector and does not exist in the reference detector and if a concentration of hydrogen existing in the reference detector is greater than a predetermined concentration, in the abnormal output mode, the output device outputs a signal indicating that an error exists in both the reference detector and the regular detector, in the intermittent output mode, the output device outputs alternately the signal indicating that no error exists in the reference detector and the signal indicating that an error exists in the regular detector if the concentration of hydrogen existing in the reference detector is lower than the predetermined concentration.

7. An output processing method according to claim 6, wherein
the output unit does not output the abnormal output when normal output satisfies a predetermined requirement.

8. An output processing method according to claim 6, wherein
the output unit adjusts the interval of the output of the abnormal output based on the level of the error on said one of the gas detectors, in which the error exists.

9. An output processing method according to claim 6, wherein
the output unit adjusts the intensity of the output of the abnormal output based on the level of the error on said one of the gas detectors, in which the error exists.

* * * * *